US00PP12380P2

(12) United States Plant Patent
Drewlow

(10) Patent No.: US PP12,380 P2
(45) Date of Patent: Feb. 5, 2002

(54) KALANCHOE PLANT NAMED 'FOREVER MIDI PINK STARLET'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/568,414

(22) Filed: May 10, 2000

(51) Int. Cl.[7] ..... A01H 5/00
(52) U.S. Cl. ..... Plt./335

(58) Field of Search ..... Plt./335, 339

*Primary Examiner*—Bruce R. Campell
*Assistant Examiner*—Michelle Kizilkaya
(74) *Attorney, Agent, or Firm*—Webb Ziesenheim Logsdon & Orkin & Hanson, P.C.

(57) ABSTRACT

A new Kalanchoe cultivar named 'Forever Midi Pink Starlet' characterized by the combined features of the unique color pattern on flowers with a light lavender-pink area in center parts of petals and deeper lavender-purple at edge and center of petals, excellent basal branching, and superior keeping quality.

1 Drawing Sheet

The present invention relates to a new and distinct cultivar of Kalanchoe plant, botanically known as *Kananchoe blossfeldiana*, and known by the cultivar name 'Forever Midi Pink Starlet'. 'Forever Midi Pink Starlet' was developed in a controlled breeding program in Ashtabula, Ohio by crossing Mikkelsen Seedling No. 93-336-2 (seed parent) (unpatented) with Mikkelsen Seedling No. 93-223-8 (pollen parent) (unpatented). The seed and pollen parents are proprietary breeding lines which have not been sold or made publicly available in this country. The plant is perennial, but typically used as an annual in the floriculture industry.

Asexual reproduction by stem cuttings taken by the inventor in Lompoc, Calif. has shown that the unique features of this new Kalanchoe are stabilized and are reproduced true to type in successive propagations.

The following characteristics distinguish the new Kalanchoe from other cultivated Kalanchoes of this type known to the inventor. The characteristics are described with comparative reference to the unpatented cultivars Pablo and Tencotta.

1. 'Forever Midi Pink Starlet' has a pattern with dark lavender-purple at edge and center of petal near base and light lavender pink in center, 'Pablo' has pink flowers with pink tips and 'Tencotta' has dark brown star in center of petal and orange at edge.

2. 'Forever Midi Pink Starlet' has excellent basal branching with nodes breaking all the way to base of plant while 'Pablo' does not have basal branching and 'Tencotta' is intermediate.

3. 'Forever Midi Pink Starlet' has narrower leaves (4.5 to 5 cm wide) while 'Pablo' and 'Tencotta' have 6.5 to 7 cm wide leaves with all three cultivars having leaf lengths of 9 to 10 cm.

4. 'Forever Midi Pink Starlet' has a 8.5 to 9 week response time which is similar to 'Pablo' but earlier than 'Tencotta' which is a 10 week cultivar.

5. 'Forever Midi Pink Starlet' has superior keeping quality of the open floral display lasting a week or more longer than 'Pablo' and 'Tencotta'.

6. 'Forever Midi Pink Starlet' has more rounded lobing of the leaf edge while 'Pablo' and 'Tencotta' each have more pointed lobing.

7. 'Forever Midi Pink Starlet' has Yellow-Green Group 146B sepals while 'Pablo' has Yellow-Green Group 146D sepals.

The accompanying colored photograph illustrates the overall appearance of this cultivar, as described in detail below, taken as a face view of the plant and showing the colors as true as it is reasonably possible to obtain in a colored reproduction of this type.

The following is a detailed description of the new cultivar, based on plants produced in greenhouses in Lompoc, Calif. during the Winter season of the year. Plants were grown in 10 cm pots and measurements were taken 13 weeks after rooted cuttings were planted. Height measurements were taken from the soil line of the container. The plants were grown at 16° C. night temperatures, 3000–4000 foot candles of light, and 200 ppm nitrogen, 75 ppm potassium, and 200 ppm phosphorous nutritional levels, with trace elements added. Habit of growth, foliage coloration, size of leaves, and peduncle length will be greatly influenced by nutritional and environmental conditions.

Color references are made to The Royal Horticultural Society Colour Chart except where general terms of ordinary dictionary significance are used.

Parentage: A controlled cross between female parent Mikkelsen Seedling No. 93-336-2 and male parent Mikkelsen Seedling No. 93-223-8.

Propagation:

(*A*) *Type cutting.*—Stem tip cuttings up to 3 cm long.

(*B*) *Time to root.*—10 days at 21° C. summer; 12 days at 21° C. winter.

(*C*) *Rooting habit.*—Fine, fibrous, abundant.

Plant description:

*Habit and form of growth.*—Compact, semi-mounded, excellent basal branching; flower clusters bloom above foliage. Environment and use of growth regulators will play a role in final height. Average height is 20 cm and average width is 20 cm. Internode length is typically 12 mm. Main stem diameter is 10 mm, stem texture is smooth, glabrous and stem color is Yellow-Green Group 147A.

*Foliage description.*—Leaves simple and opposite. Leaves are petiolate and petioles are Yellow-Green Group 147A having a length of 15 mm and a width of 4 mm. Size: Average, full grown leaves on a plant when grown in a 10 cm pot are 9 to 10 cm long and 4.5 to 5 cm wide. Shape: Ovate with obtuse apex and acute base. Texture: Glabrous; coriaceous and succulent. Margin: Crennate; shallow lobed. Color: Young foliage top side is Yellow-Green Group 147A, underside is Yellow-Green Group 147B; mature foliage top side is Yellow-Green Group 147A, underside is Yellow-Green Group 146A.

*Branching.*—Average number of lateral branches is 8. The average lateral branch length is 15 cm and average lateral branch diameter is 5 mm. The branch texture is smooth, glabrous and color is Yellow-Green Group 147A.

Flowering description:

*Flowering habits.*—Inflorescence is a compound dichasial cyme. Terminal flower on main axis opens first followed by the terminal flowers of the side branches, continuing with the subsequent development of branches in the inflorescence. Inflorescence is made up of the main stem and up to 8 or more lateral branches depending on growing schedule followed.

*Natural flowering season.*—Early January. Flowering time under controlled daylength (10 hours daylight, 14 hours darkness) at 20° C. in summer is 8.5 to 9 weeks; in winter is 10 to 10.5 weeks. Flowering time depends on temperature, light intensity and other growing conditions.

*Flower buds.*—Oblong, up to 10 mm long before showing color, developing to tubular as flower petals mature; sheathed in four (4) sepals colored yellow-green. Sepals are individual with a lanceolate shape. Sepals are 8 mm long and 2 mm wide.

*Flowers borne.*—Compound dichasial cyme with primary peduncle being 4 mm in diameter just below the first branch of the inflorescence; length of peduncle will vary depending on growing conditions. The average number of peduncles is 10 with an average length of 12 cm, average diameter of 4 mm, smooth, glabrous texture, and Yellow-Green Group 147A color. The average number of pedicels is 250 with an average of 3 mm, average diameter of 1 mm, smooth, glabrous texture, and Yellow-Green Group 147A color. Pedicels vary in length depending on where they are in the inflorescence.

*Quantity of flowers.*—Numerous flowers on the main stem plus the 8 or more lateral branches will have 25 or more flowers each. Approximate time period for bloom lastingness is 4 to 6 weeks. The florets are flat in shape.

*Petals.*—Shape: Almost rounded, top cuspidate. Color: Top side when opening is Orange-White Group 159A with areas of Red-Purple Group 61C at edge and center of petal, deepening to Red Group 56B with areas of Red-Purple Group 63A. Underside is Red Group 56C with areas of Red-Purple Group 64C. Number of petals: 4.

*Reproductive organs.*—Stamens: 8 in number, with an average size of 3 mm not fused to the petal. Anthers: Flat, elliptical in shape, yellow-green in color. Filament color: Yellow-green. Pollen: Abundant, yellow. Pistils: Stigma: Flat in shape, mature color is white. Style color: Light green. Ovaries: 4 in number, size 6 mm, green color.

*Fertility.*—The plants are fertile, but do not normally set seed under greenhouse or garden conditions, unless in a controlled crossing program.

Disease resistance: 'Forever Midi Pink Starlet' has shown resistance to powdery mildew. No disease problems have been observed to date.

OTHER IMPORTANT CHARACTERISTICS

1. 'Forever Midi Pink Starlet' has a unique color pattern on flowers with a light lavender pink area in center of parts of petals and deeper lavender-purple at edge and center of petals.

2. Due to highly branched compact growth habit, the plant can be finished in a 10 cm pot without use of growth regulators.

3. Pinching is not required or recommended.

I claim:

1. A new and distinct cultivar of Kalanchoe plant named 'Forever Midi Pink Starlet', as illustrated and described.

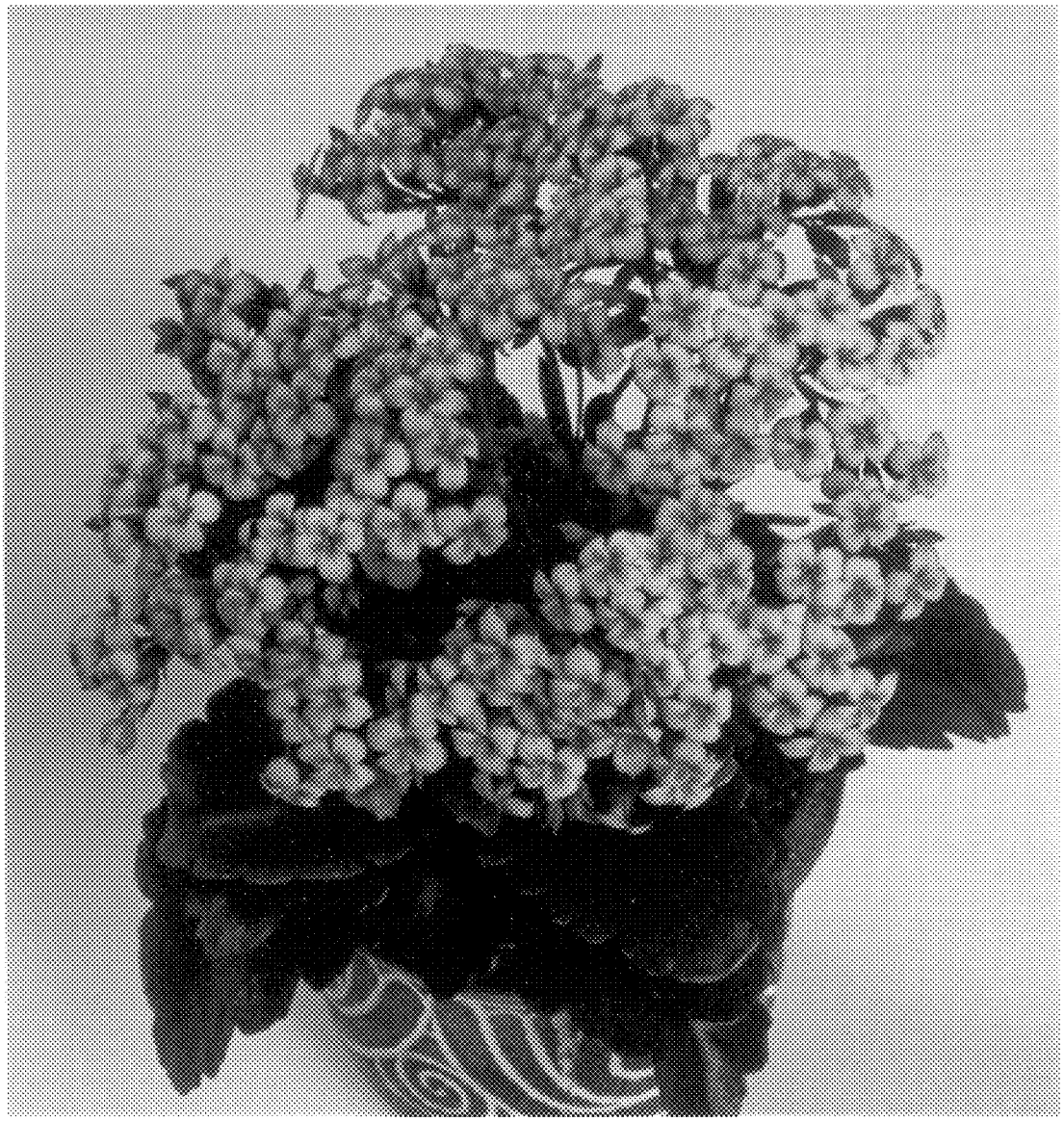

* * * * *